United States Patent [19]

Riley

[11] Patent Number: 4,871,386
[45] Date of Patent: * Oct. 3, 1989

[54] BIOLOGICAL CONTROL OF WILD POINSETTIA AND OTHER WEEDY SPURGES WITH A FUNGAL PATHOGEN

[75] Inventor: Joe A. Riley, Ruston, La.

[73] Assignee: Mycogen Corporation, San Diego, Calif.

[*] Notice: The portion of the term of this patent subsequent to Jul. 5, 2005 has been disclaimed.

[21] Appl. No.: 70,008

[22] Filed: Jul. 6, 1987

Related U.S. Application Data

[63] Continuation-in-part of Ser. No. 856,614, Apr. 25, 1986, Pat. No. 4,755,208.

[51] Int. Cl.$^4$ .......................... A01N 63/00; C12N 1/14
[52] U.S. Cl. .......................................... 71/79; 435/254; 435/911; 424/93
[58] Field of Search ................... 424/93; 435/254, 911; 71/79

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,097,261 | 6/1978 | Conway et al. | 71/66 |
| 4,390,360 | 6/1983 | Walker | 71/79 |
| 4,419,120 | 12/1983 | Walker | 71/79 |
| 4,755,208 | 7/1988 | Riley et al. | 71/79 |

OTHER PUBLICATIONS

Akobundu, I. Okezie [1982] "Weed Control in Cowpea (*Vigna unguiculata*) in the Humid Tropics," Weed Science 30:331-334.

Bannon, J. S., Baker, J. B., and Rogers, R. L. [1978] "Germination of Wild Poinsettia (*Euphorbia heterophylla*)," Weed Science 26:221-225.

Harger, Thomas R. and Nester, Paul R. [1980] "Wild Poinsettia: A Major Soybean Weed," Louisiana Agric. 23(3):4-5.

Langston, V. B. and Harger, T. R. [1983] "Potential for Late Season Infestation by Wild Poinsettia," Proc. South. Weed Sci. Soc. 36:77.

*Primary Examiner*—Thomas G. Wiseman
*Assistant Examiner*—Richard C. Peet
*Attorney, Agent, or Firm*—Roman Saliwanchik; David R. Saliwanchik

[57] ABSTRACT

The subject invention concerns a novel bioherbicide and its use to control major weeds found in many fields in the United States. Specifically, *Alternaria euphorbiicola* Simmons and Engelhard, having the identifying characteristics of culture deposit NRRL 18227, in an agricultural composition, can be used to effectively control wild poinsettia and weedy spurges. Further, *Alternaria euphorbiicola* Simmons and Engelhard, having the identifying characteristics of deposit NRRL 18227, in a mixture with *Alternaria cassiae*, can be used to control wild poinsettia and weedy spurges and other undesired vegetation, such as sicklepod, showy crotalaria, and coffee senna. Further, the bioherbicide of the invention can be mixed with a chemical herbicide to increase weed control.

10 Claims, No Drawings

BIOLOGICAL CONTROL OF WILD POINSETTIA AND OTHER WEEDY SPURGES WITH A FUNGAL PATHOGEN

This is a continuation-in-part of our copending application Ser. No. 856,614, filed Apr. 25, 1986, now U.S. Pat. No. 4,755,208.

BACKGROUND OF THE INVENTION

1. Field of the Invention

The instant invention is a method for the control of undersirable plants by use of plant pathogens.

2. Description of the Prior Art

The merits for using plant pathogens to control weeds in annual crops have been discussed previously for two Colletotrichum spp. (Daniel, et al. U.S. Pat. No. 3,849,104 and Templeton, U.S. Pat. No. 3,999,973). The anthracnose fungus *Colletotrichum gloeosporioides* has been used to control the weed northern jointvetch, and another strain of this fungus has been used to control winged water-primrose. Colletotrichum malvarum has been used to control prickly sida. These three pathogens have been combined to control all three target weeds at once. In other work the fungus *Alternaria cassiae* (U.S. Pat. No. 4,390,360) has been used to control sicklepod, coffee senna, and showy crotalaria. Another fungus *Fusarium lateritium* (U.S. Pat. No. 4,419,120) has been used to control pirckly sida, velvetleaf and spurred anoda. Included in this same patent, the synergistic interaction between *F. lateritium* and *Alternaria macrospora* has been used for contorl of spurred anoda.

*Cercospora rodmanii* has been used to control waterhyacinth (U.S. Pat. No. 4,097,261) and *Phytophthora palmavora* has been commercially developed as a biological herbicide for stranglervine.

Wild poinsettia (*Euphorbia heterophylla* L.) is a major weed problem in portions of the southern United States, Brazil, Colombia, Peru, Nigeria, and in several other countries which have tropical or subtropical climates (Akobundu, I.O. [1982]Weed Science 30:331–334; Bannon, J. S., Baker, J. B. and Rogers, R. L. [1978]Weed Science 26:221–225; Reed, C. F. [1971]U.S. Dept. Agric. Handbook No. 498). This annual species reduces yield through direct competition with crop plants and interferes with harvesting. The plants produce a sticky latex sap that interferes with harvesting and reduces seed quality of soybeans by increasing moisture levels and trash accumulation (Harger, T. R. and Nester, P. R. [1980] Louisiana Agric. 23(3):4–5; Langston, V.B. and Harger, T. R. [1983] Proc. South. Weed Sci. Soc. 36:77).

Wild poinsettia or "painted leaf" is an annular herb that commonly has two leaf shapes; long, narrow leaves, and wider, lobed leaves. Both leaf shapes can occur on the same plants. As plants mature, the foliage develops numerous dark spots (Bannon et al., spura).

Seed germination is greatly influenced by light and temperature. Seeds remain viable in soil for extended periods of time, and maximum germination rates occur as the soil temperatures increase in late spring and early summer (Bannon et al. and Harger et al., supra).

Wild poinsettia is difficult and expensive to control using conventional weed control practices. Planting soybeans early in the growing season before wild poinsettia seedlings emerge has been shown to provide some control. Chemical herbicides recommended for control of wild poinsettia include metribuzin, linuron, acifluorfen, and dinoseb. Multiple herbicide applications are often necessary for satisfactory control (Harger et al., supra).

There is a need to have an effective means for the biological control of wild poinsettia and weedy spurges. Such a means would, advantageously, eliminate, or at least reduce the use of chemical agents to control these weeds. It is well known that the extensive use of chemicals to control weeds over the last twenty years has placed a heavy burden on the ecosystem, resulting in contamination of groundwater, lakes, rivers, etc. The substitution of biological control agents for many of these chemicals is recognized as a solution to this chemical contamination problem.

BRIEF SUMMARY OF THE INVENTION

The subject invention concerns the use of a novel isolate of the fungus *Alternaria euphorbiicola* Simmons and Engelhard, Isolate No. 241, to control the noxious weeds wild poinsettia and weedy spurges. The novel isolate of the subject invention is also active against Florida beggarweed (*Desmodium tortuosum*) and prickly sida (*Sida spinosa*). Advantageously, this fungus controls these weeds when present among desired field crops without damaging the crops. For example, the novel *Alternaria euphorbiicola* isolate of the invention can be used to control wild poinsettia found in a field planted with soybeans. Also, this novel isolate can be used to control spotted spurge present in fields of soybeans, cotton, and other agronomic crops. Though the prime use of the novel *A. euphorbiicola* isolate is to control wild poinsettia and weedy spurges in fields planted with desired crops, this fungus also can be used to control these weeds along roadways, river banks and lake shores, in recreational areas, and the like.

DETAILED DESCRIPTION OF THE INVENTION

The novel *A. euphorbiicola* isolate of the subject invention is closely related to *Alternaria euphorbiicola*, NRRL 18056, disclosed and claimed in our pending U.S. patent application Ser. No. 856,614, now U.S. Pat. No. 4,755,208. However, the isolate of the subject invention is clearly distinguished from *A. euphorbiicola*, NRRL 18056, by activity against certain weeds which NRRL 18056 has not shown activity against. In particular, Isolate #241 of the subject invention is active against Florida beggarweed and prickly sida, whereas no such activity has been shown for NRRL 18056. Thus this difference in host range clearly differentiates these two isolate of *A. euphorbiicola*. The comparison of the host range for NRRL 18056 and NRRL 18227 is shown in Table 1.

The culture disclosed in this application has been deposited in the Agricultural Research Service Patent Culture Collection (NRRL), Northern Regional Research Center, 1815 North University Street, Peoria, Ill. 61604, U.S.A.

| Culture | Repository No. | Deposit Date |
|---|---|---|
| *Alternaria euphoribiicola* Mycogen #241 | NRRL 18227 | June 19, 1987 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncomtaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should be depository be unable to furnish a sample when requested, due to the condition of the deposit. All restrictions on the availability to the public of the subject culture deposit will be irrevocably removed upon the granting of a patent disclosing it.

Following are examples which illustrate the process of the invention, including the best mode. These examples should not be construed as limiting. All solvent mixture proportions are by volume unless otherwise noted.

EXAMPLE 1 INOCULUM PRODUCTION

Inoculum of *A. euphorbiicola*, NRRL 18227, for tests is produced in petri dishes containing vegetable juice agar (V-8 JUICE, Campbell Soup Company) in accordance with the method of P.M. Miller disclosed in Phytopathology 45:461-2 (1955) in an article entitled "V-8 juice agar as a general-purpose medium for fungi and bacteria." The cultures are incubated at 25° C. with a 12-hr diurnal light cycle supplied by two, 40-w cool white fluorescent bulbs that are suspended 20 cm above the cultures. The 12-Hr dark cycle temperature is 19° C. To produce large quantities of inoculum, conidia from petri-dish-grown cultures are used to inoculate 500 ml of sterile liquid growth medium contained in cotton-plugged 1000 ml Erlenmeyer flasks. The liquid growth medium consists of soyflour, 15 g/L; corn meal, 15 g/L; sucrose, 30 g/L; calcium carbonate, 3 g/L; and distilled water.

The cultures are incubated at 25° C. on a rotary shaker at 160 rpm. After 4 to 5 days, the mycelial cultures are harvested and homogenized in a Waring Blendor for 30 sec. The mycelial homogenate is poured to a depth of 2 to 4 mm into shallow trays, and exposed to light from 250-w sunlamps for 5-15 min every 12 hr for 72 hr. The spores are vacuumed from the surface of the mycelial mat and stored at 4° C. This sporulation procedure has been described in H. L. Walker and J. A. Riley (1982) Weed Sci. 30:651-654.

Granular preparations containing mycelia and conidia are prepared using the sodium alginate process described by H. L. Walker and W. J. Connick, Jr. (1983) Weed Sci. 31:333-338.

Mycelial fragment preparations are prepared by growing the fungus in liquid growth medium consisting of soyflour, 45 g/L; corn meal, 30 g/L; soluble starch, 15 g/L; sucrose, 30 g/L; calcium carbonate, 3 g/L; and distilled water. The cultures are shown in Erlenmeyer flasks at 25° C. and 160 rpm. The mycelium is harvested 8 days after inoculation, and homogenized for 30 sec in a Waring Blendor. Kaolin clay (1% w/v) is added, and the mycelial-clay mixture is homogenized for 15 sec. The mixture is centrifuged 1460 xg for 10 min and the supernatant is decanted. The mycelium-clay pellet is placed on filter paper and dried for 5 to 7 days at 4° C. The dried cake is processed through a Wiley mill (Arthur H. Thomas Company, Philadelphia, Pa.) with a 20 mesh screen and the resulting preparation is stored at 4° C.

EXAMPLE 2 HOST RANGE AND EPIDEMIOLOGY

The plant species included in the greenhouse studies are listed in Table 1. Plants are grown in a commercial potting mix (Mix No. 2, Ball Seed Company, West Chicago, Ill.) in peat strips that contain 12 plants each. Temperatures range from 28° to 32° C. with 40 to 60% relative humidity. The day length is approximately 12 hr.

Plants in the cotyledon to third leaf stage of growth are sprayed to run off with inoculum applied with an atomizer. Inoculation mixtures contain 0.05% (v/v) surfactant polyoxyethylene (20) sorbitan monooleate in distilled water and $1 \times 10^5$ spores/ml. Control plants are sprayed with water and 0.05% surfactant only. All plants are placed in dew chambers for 20 hr at 25° C. The plants then are moved to greenhouse benches and evaluated daily for 14 days. All tests are repeated on at least two dates, and 12 plants are used for each treatment in each test.

The fungus is pathogenic and highly virulent to wild poinsettia seedlings. Most seedlings in the cotyledon to fourth leaf stage of growth are killed 2 to 7 days after inoculation. The pathogen produces dark brown to black lesions 1-3 mm in diam on the leaves and stems within 2 days. The lesions enlarge with time on any remining plants and produce severe stem canker and defoliation within 7 days. Several other weedy spurge species appear to be as susceptible as wild poinsettia to the pathogen. Also, the weeds Florida beggarweed and prickly sida are susceptible to the pathogen of the invention. Most representative crop and weed species were resistant to the pathogen; however, phytotoxic damage is occasionally observed on inoculated leaves of several species (Table 1). Phytotoxic symptoms range from flecking to a marginal or interveinal "burn" of inoculated leaves. These symptoms appear within 48 to 72 hr after inoculation and do not increase in number or severity with time. Succulent tissues are most susceptible to damage. The phytotoxicity is attributed to the high concentrations of conidia contained in the inoculation mixtures. Phytotoxic injury is not observed in every test and this injury is never observed on the control plants.

Wild poinsettia plants in all stages of growth are infected by the fungus; however, plants in the fourth leaf growth stage and younger are most severely damaged.

The fungus infects plants within a dew period temperature range of 10° to 35° C. At 25° C., the fungus infects with dew periods ranging from 0 to 24 hr, and inoculum levels of 6,000 to 200,000 spores per ml. See Tables 2-5 for test results.

This foliar pathogen can be formulated and applied to the target weeds as a spray (wettable powder) or as granules that consist of the fungus and a carrier such as vermiculite, corn cob grits, or clay. Advantageously, preemergence or postemergence applications of granules can be used. The granular formulation of a foliar pathogen for soil application for preemergence weed control is unexpected because soilinhabiting organisms compete with the pathogen.

The preferred liquid carrier is water, and the spore concentrate is dispersed to make a concentration of from about $1 \times 10^4$ to about $1 \times 10^6$ spores/ml.

Spores of *A. euphorbiicola*, NRRL 18227, can be mixed with those of *Alternaria cassiage* to enlarge the scope of control of undesirable vegetation. For example, this mixture can be used to control both wild poinsettia and sicklepod (*Cassia obtusifolia*), two troublesome weeds in the Southeast. Further, spores of *A. euphorbiicola*, NRRL 18227, can be mixed with those of *A. cassiae* to control wild poinsettia and coffee senna. The use of *A. cassiae* to control sicklepod, showy crotalaria and coffee senna is disclosed in U.S. Pat. No. 4,390,360, which is incorporated herein by reference thereto. The culture, means of growing, and application to these weeds disclosed in U.S. Pat. No. 4,390,360 can be used herein. Mixtures of *A. euphorbiicola*, NRRL 18227, and *A. cassiae*, for example, *A. cassiae* NRRL 12533, can be made by methods well known in the art, utilizing the disclosure of U.S. Pat. No. 4,390,360 and that contained herein.

Through spores are the preferred form of the fungi, the fungi also can be formulated as fragmented mycelia and applied as foliar sprays.

Spores of mycelial fragments of *A. euphorbiicola*, NRRL 18227, can be combined with various chemical additives, particularly chemical herbicides, to increase weed control. These additives would be expected to broaden the spectrum of activity so that additional species of weeds can be controlled. Application rates of these chemicals would be expected to be less than or equal to the rates recommended for conventional use.

Examples of these chemicals include but are not limited to the following;

| Trade Name[1] | Chemical Name | Common Name |
|---|---|---|
| Alanap (B) | 2-[(1-naphthalenylamino)carbonyl] benzoic acid | naptalam |
| Basagran (B) | Sodium salt of (3-isopropyl-1 H—2,1,3-bentzothiadiazin-4 (3H)—one 2,2-dioxide) | bentazon sodium salt |
| Basta (B&G) | Ammonium-DL-homoalanin-4-yl (methyl) phosphinate | glufosinate ammonium |
| Blazer (B&G) | Sodium 5-[2-chloro-4-trifluoro methyl)phenoxy]-2-nitrobenzoate | acifluorfen sodium salt |
| Butyrac 200 (B) | 4-(2,4-Dichlorophenoxy)butyric acid | 2,4-DB |
| Cobra (B) | 1-(carboethoxy)ethyl 5-[2-chloro-4-(trifluoromethyl)phenoxy]-2-nitrobenzoate | lactofen |
| DOWPON (G) | 2,2'-dichloropropionic acid | dalapon |
| Fusilade (G) | Butyl(R—S)—2-[4-[[5-(trifluoro-methyl)-2-pyridinyl]oxy]phenoxy] propanoate | fluazifop |
| Hoelon (G) | Methyl 2-[4-(2,4-dichlorophenoxy) phenoxy]propanoate | diclofop methyl |
| Premerge 3 (B&G) | Dinoseb(2-sec-butyl-4,6-dinitro-phenol) as the alkanolamine salts | dinoseb |
| Roundup (B&G) | Isopropylamine salt of N—glyphosate (phosphonomethyl)glycine | |
| Scepter (B) | Ammonium salt of 2-[4,5-Dihydro-4-methyl ethyl)-5-oxo-1H—imidazol-2-yl]-3-quinoline carboxylic acid | imazaquin |
| Classic | 2-(([(4-chloro-6-methox-pyrimidine-2-yl)amino carbonyl] amino sulfonyl))benzoic acid ethyl ester | DPX-F6025 |
| Dual 8E | 2-chloro-N—(2-ethyl-6-methyl-phenyl-N—(2-methoxy-1-methyl-ethyl)acetamide | metolachlor |
| Poast | 2-[1-(ethoxyimino)butyl]-5[2-(ethylthio)propyl]-3-hydroxy-2-cyclohexen-1 one | sethoxydim |
| Sencor | 4-Amino-6-(1,1-dimethylethyl)-3-(methylthio)-1,2,4,-triazin-5(4H)—one | metribuzin |
| Lorox, Linurex | 3-(3,4-dichlorophenyl)-1-methoxy-1-methylurea | linuron |
| Karmex | 3-(3,4-dichlorophenyl)-1,1-dimethylurea | diuron |
| Surflan | 3,5-Dinitro-$N^4N^4$—dipropyl sulfanilamide | oryzalin |
| B-Nine | Daminozide butanedioic acid mono(2,2-dimethylhydrazide) | Alar |
| Dropp | N—phenyl-N'—1,2,3-thiadiazol-5 yl urea | thidiazuron |
| Embark | Diethanolamine salt of (N—[2,4-dimethyl-5-[[(trifluoromethyl)-sulfonyl]amino]phenyl]acetamide | mefluidide |
| Stik | 1-Naphthaleneacetic acid | NAA |

[1]The notation in parentheses indicates the activity of the herbicide (B = broadleaf control, G = grass control, and B&G = broadleaf and grass control.

TABLE 1

Comparison of Plant Host Range for *Alternaria euphorbiicola*, NRRL 18056, and *Alternaria euphorbiicola*, NRRL 18227[a].

| Family Species | Disease Rating[b] | |
|---|---|---|
| | NRRL 18056 | NRRL 18227 |
| Brassicaceae | | |
| Turnip (*Brassica rapa*) 'purple Top' | R | R+ |
| Cucurbitaceae | | |
| Watermelon (*Citrullus vulgaris*) 'Charleston Grey' | R | R |
| Euphorbiaceae | | |
| Poinsettia (*Euphorbia pulcherrima*) 'Gutbier V-14 Glory' | S | S |
| Poinsettia (*Euphorbia heterophylla*) Mexican Fire Plant | S | S |
| Poinsettia (*Euphorbia heterophylla*) Wild Poinsettia | S | S |
| Spurge (*Euphorbia hyssopifolia*) | S | S |
| Spurge (*Euphorbia polychroma*) | S | S |
| Spurge (*Euphorbia supina*) Prostrate Spurge | S | — |
| Spurge (*Euphorbia humistrata*) Prostrate Spurge | — | S |
| Poaceae | | |
| Corn (*Zea mays*) 'Silver Queen' | R | R+ |
| 'Florida State' | — | R+ |
| Johnsongrass (*Sorghum halepense*) | R | R |
| Fabaceae | | |
| Beggarweed (*Desmodium tortuosum*) Florida Beggarweed | R+ | S |
| Lima bean (*Phaseolus limensis*) 'Jackson Wonder' | R | R |
| Peanut (*Arachis hypogaea*) 'Tennessee Red' | — | R |
| Cowpea (*Vigna sinensis*) 'California Pinkeye' | R | R+ |
| Sicklepod (*Cassia obtusifolia*) | R+ | R+ |
| Soybean (*Glycine max*) 'Forrest' | R | R+ |
| 'Centennial' | — | R+ |
| 'Hill' | R | — |
| Malvaceae | | |
| Cotton (*Gossypium hirsutum*) 'DPL-61' | R+ | — |
| 'Stoneville 506' | R+ | — |
| 'DPL-90' | — | R++ |
| 'Pima' | — | R++ |

TABLE 1-continued

Comparison of Plant Host Range for *Alternaria euphorbiicola*, NRRL 18056, and *Alternaria euphorbiicola*, NRRL 18227[a].

| Family Species | Disease Rating[b] | |
|---|---|---|
| | NRRL 18056 | NRRL 18227 |
| 'Stoneville 825' | — | R++ |
| 'Camd. E' | — | S |
| Okra (*Abelmoschus esculentus*) | R+ | S |
| 'Clemson Spineless' | | |
| Prickley sida (*Sida spinosa*) | R+ | S |
| Velvetleaf (*Abutilon theophrasti*) | R | R+ |
| Solanaceae | | |
| Tomato (*Lycopersicon esculentum*) | | |
| 'Better Boy' | R | — |
| 'Manalucie' | R | R |
| 'Rutgers' | R | R |

[a]Plants of each species were sprayed with inoculum containing 1 × 10$^5$ spores/ml. Data were collected 14 days after inoculation.
[b]R = resistant and S = susceptible to the pathogen; + = phytotoxic injury by the pathogen limited to flecking or small, non-damaging burning of the leaves; ++ = some stunting with larger, non-spreading necrotic areas on the leaves.

TABLE 2

Effect of Dew-Period Duration on the Control of Hyssop Spurge by *Alternaria euphorbiicola*, NRRL 18227[a].

| Length of Dew-Period (hr) | Plants Killed (%) |
|---|---|
| 0 | 0 |
| 2 | 0 |
| 4 | 63 |
| 6 | 100 |
| 8 | 100 |

[a]Twenty-four plants 2–4 cm in height were sprayed to wetness with a suspension that contained 1 × 10$^5$ conidia/ml, then placed in dew chambers at 25° C. Data were collected 14 days after inoculation.

TABLE 3

Effect of Inoculum Levels on the Control of Hyssop Spurge with *Alternaria euphorbiicola*, NRRL 18227[a].

| Spore Concentration (No./ml, × 10$^3$) | Plants Killed (%) (3 reps) |
|---|---|
| 0 | 0 |
| 6.25 | 22 |
| 12.5 | 36 |
| 25 | 92 |
| 50 | 100 |
| 100 | 100 |
| 200 | 100 |

[a]Thirty-six plants 4–6 cm in height were inoculated with each spore concentration. Dew-periods were 8 hr at 25° C. Data were collected 14 days after inoculation.

TABLE 4

Effect of Growth Stage on Control of Hyssop Spurge by *Alternaria euphorbiicola*, NRRL 18227[a].

| Plant Height | Plants Killed (%) |
|---|---|
| 2 cm | 100 |
| 4 cm | 100 |
| 6 cm | 100 |
| 8 cm | 100 |
| 14 cm | 83 |
| 16 cm | 29 |

[a]Twenty-four plants at each growth stage were sprayed to wetness with a suspension containing 1 × 10$^5$ conidia/ml. Plants received an 8 hr dew period at 25° C. Data were collected 14 days after inoculation.

TABLE 5

Effect of Different Dew-Period Temperatures on the Control of Hyssop Spurge by *Alternaria euphorbiicola*, NRRL 18227[a].

| Temperature (C.) | Plants Killed (%) (3 reps) |
|---|---|
| 10 | 92 |
| 15 | 100 |
| 20 | 100 |
| 25 | 100 |
| 30 | 100 |
| 35 | 83 |

[a]Thirty-six plants were sprayed to wetness with a suspension containing 1 × 10$^5$ conidia/ml; dew-periods were 8 hr. Data were collected 14 days after inoculation.

I claim:

1. A composition for controlling wild poinsettia and weedy spurges comprising a novel isolate of the fungus *Alternaria euphorbiicola* Simmons and Engelhard, having the identifying characteristics of deposit NRRL 18227, in association with an agricultural carrier.

2. A composition, according to claim 1, wherein said weedy spurge is spotted spurge.

3. A composition, according to claim 1, wherein said *Alternaria euphorbiicola* Simmons and Engelhard, having the identifying characteristics of deposit NRRL 18227, is in the spore form at a spore concentration of from about 1 × 10$^4$ spores/ml of carrier to about 1 × 10$^6$ spores/ml of carrier.

4. A process for controlling wild poinsettia or weedy spurges which comprises applying the fungus *Alternaria euphorbiicola* Simmons and Engelhard, having the identifying characteristics of deposit NRRL 18227, onto said wild poinsettia or weedy spurges or unto the situs of said wild poinsettia or weedy spurges.

5. A composition for agricultural application for controlling wild poinsettia, weedy spurges, sicklepod, showy crotalaria and coffee senna comprising a mixture of the fungi *Alternaria euporbiicola* Simmons and Engelhard, having the identifying characteristics of deposit NRRL 18227, and *Alternaria cassiae* in association with an agricultural carrier.

6. A composition, according to claim 5, wherein said *Alternaria cassiae* is *Alternaria cassiae* NRRL 12553.

7. A composition for controlling wild poinsettia and weedy spurges comprising a novel isolate of the fungus *Alternaria euphorbiicola* Simmons and Engelhard, having the identifying characteristics of deposit NRRL 18227, in mixture with a chemical herbicide.

8. A biologically pure culture of a novel isolate of *Alternaria euphorbiicola* Simmons and Engelhard, having the identifying characteristics of deposit NRRL 18227, and having the novel properties of pathogenicity to wild poinsettia, weedy spurges, Florida beggarweed, and prickly sida.

9. A composition for controlling wild poinsettia comprising a novel isolate of the fungus *Alternaria euphorbiicola* Simmons and Engelhard, having the identifying characteristics of deposit NRRL 18227, in association with an agricultural carrier.

10. A process for controlling wild poinsettia which comprises applying the fungus *Alternaria euphorbiicola* Simmons and Engelhard, having the identifying characteristics of deposit NRRL 18227, onto said wild poinsettia or unto the situs of said wild poinsettia.

* * * * *

UNITED STATES PATENT AND TRADEMARK OFFICE
CERTIFICATE OF CORRECTION

PATENT NO. : 4,871,386

DATED : October 3, 1989

INVENTOR(S) : Joe A. Riley

It is certified that error appears in the above-identified patent and that said Letters Patent is hereby corrected as shown below:

| | | |
|---|---|---|
| Column 1: | line 28: | "pirckly" should read --prickly--. |
| | line 31: | "contorl" should read --control--. |
| | line 43: | "[1971]" should read --[1977]--. |
| | line 54: | "annular" should read --annual--. |
| | line 58: | "spura)." should read --supra).--. |
| Column 3: | line 18: | "should be depository" should read --should the depository--. |
| | line 40: | "12-Hr" should read --12-hr--. |
| | line 66: | "cultures are shown in" should read --cultures are grown in--. |
| Column 4: | line 35: | "lesions 1-3 mm" should read --lesions 1-5 mm--. |
| | line 37: | "any remining plants" should read --any remaining plants--. |

UNITED STATES PATENT AND TRADEMARK OFFICE
CERTIFICATE OF CORRECTION

PATENT NO. : 4,871,386
DATED : October 3, 1989
INVENTOR(S) : Joe A. Riley

It is certified that error appears in the above–identified patent and that said Letters Patent is hereby corrected as shown below:

Column 5:
- line 9: "of Alternaria cassiage" should read --of Alternaria cassiae--.
- line 26: "Through spores" should read --Though spores--.
- line 29: "Spores of mycelial" should read --Spores or mycelial--.
- line 62: "salt of N-glyphosate" should read --salt of N--- (glyphosate should be moved to the next column).

Column 6:
- line 6: "phenyl-N-" should read --phenyl)-N---.
- line 16.5 "dipropyl" should read --dipropyl- --.
- line 35.5: "'purple Top'" should read --'Purple Top'--.

Signed and Sealed this

Nineteenth Day of February, 1991

Attest:

HARRY F. MANBECK, JR.

Attesting Officer

Commissioner of Patents and Trademarks